United States Patent [19]

Evers

[11] Patent Number: 5,298,528

[45] Date of Patent: Mar. 29, 1994

[54] INSECT REPELLENT

[75] Inventor: Hans Evers, Sodertalje, Sweden

[73] Assignee: Baker Cummins Dermatologicals, Inc., Miami, Fla.

[21] Appl. No.: 957,435

[22] Filed: Oct. 6, 1992

[30] Foreign Application Priority Data

Oct. 7, 1991 [SE] Sweden ................. 9102890

[51] Int. Cl.$^5$ .................. A01N 37/18; A01N 33/02; A01N 25/00
[52] U.S. Cl. .................... 514/626; 514/650; 514/651; 514/919; 424/405; 424/DIG. 10
[58] Field of Search ............ 424/405, DIG. 10, 78.02; 514/919, 354, 626, 651, 650, 54

[56] References Cited

U.S. PATENT DOCUMENTS 4,970,220 11/1990 Chaussee ..................... 514/358

FOREIGN PATENT DOCUMENTS

| | | |
|---|---|---|
| 0156540 | 10/1985 | European Pat. Off. |
| 0208523 | 1/1987 | European Pat. Off. |
| 2576180 | 10/1984 | France |
| WO90/05542 | 5/1990 | PCT Int'l Appl. |
| 8804214 | 11/1988 | Sweden |

OTHER PUBLICATIONS

Chemical Abstracts, 84(15):10099s (1976).
Chemical Abstracts, 84(25):174480f (1976).
E. W. Schaffer, Jr., et al, "The acute oral toxicity, repellency, and hazard potential of 998 chemicals to one or more species of wild and domestic birds", pp. 355–382, Arch. Environm. Contam. Toxicol, 12, 355–382 (1983).
Chemical Abstracts, 102(21):180768n (1985).
Viktorov–Nabokov et al., *Chem. Abstracts,* 84:39641u (1976).
Viktorov–Nabokov et al., *Chem. Abstracts,* 94:151823n (1981).
Osborne, *Pestic. Biochem. and Physiol.,* 23:190–204 (1985).
Erdos, *Chem. Abstracts,* 104:16547k (1986).

*Primary Examiner*—Douglas W. Robinson
*Assistant Examiner*—Maria L. Osoteo
*Attorney, Agent, or Firm*—Kirschstein, Ottinger, Israel & Schiffmiller

[57] ABSTRACT

An insect repellent composition for against mosquitoes or other insects that attack man and or warm-blooded animals contains up to 5% by weight of a local anaesthetic selected from the group comprising alkyl p-aminobenzoate (I), arylamide of 2-aminoacetic acid (II), 2-aminoalkyl aryl ether (III), 2-aminoalkyl p-aminobensoate (IV) and mixtures thereof. Particularly preferred is lidocaine and a mixture of lidocaine and prilocaine.

8 Claims, No Drawings

INSECT REPELLENT

The present invention relates to an insect repellent, particularly a repellent to be used against mosquitoes or other insects, particularly certain fly species, that attack man and or warm-blooded animals.

Many substances have been suggested through the years to be used as active ingredients in repellent compositions against mosquitoes, e.g. dimethyl phthalate and N,N-diethyl-m-toluamide (DEET). After application of such compositions to the skin, the repellent is released by evaporation over a period of time. This process, however, is often quite rapid thus reducing their usefulness. Furthermore, it has been shown that the known active principles with insect repellent properties are easily absorbed by the skin and may cause dermal allergies, skin irritation, etc. A further drawback is that they are quite easily physically removed from the skin. Some of the known insect-repellent compounds possess a distinct and not very pleasant odor.

In order to prolong their effect attempts have been made to incorporate the active ingredients with insect-repellent properties in different forms of preparations.

U.S. Pat. No. 4,477,467 discloses an insect repellent composition containing DEET as active agent in combination with an aromatic carrier. This composition is considered to provide increased resistance against dermal absorption by the formation of a complex including the active principle.

U.S. Pat. No. 3,590,118 discloses a film-forming composition containing known repellents incorporated in water-soluble polymer residues. The time period of effective protection thereby is extended to about 24 hours. However, the film formed on the skin by this composition may easily break and the repellent effect thereby be considerably reduced.

In the present context, "insect repellent" denotes an agent that prevents insects feeding on humans, mammals or birds from penetrating the human or animal skin. This implies that the insect to be repelled may access the skin but will not feed on it.

An aim with the present invention is to provide an insect repellent composition whith superior properties compared with known insect repellent compositions, particularly in respect of effect, duration of protection and absorption by the skin and skin irritation.

According to the invention, there is provided an insect repellent composition containing as active ingredient a local anaesthetic selected from the group comprising alkyl p-aminobenzoate (I), arylamide of 2-aminoacetic acid (II), 2-aminoalkyl aryl ether (III), 2-aminoalkyl p-aminobenzoate (IV) and mixtures thereof.

It is preferred for the alkyl p-aminobenzoate (I) to be benzocaine (R=CH$_2$CH$_3$).

It is preferred for the arylamide of 2-aminoacetic acid (II) to be selected from the group comprising lidocaine (II; R=CH$_3$, R$^1$=H, R$^2$, R$^3$=C$_2$H$_5$), prilocaine (II; R=H, R$^1$=—CH$_3$, R$^2$=CH$_2$CH$_2$CH$_3$, R$^3$=H), etidocaine (II; R=CH$_3$; R$^1$=C$_2$H$_5$, R$^2$=C$_2$H$_5$, R$^3$=CH$_2$CH$_2$CH$_3$) and mepivacaine (IIa; R=CH$_3$, R$^1$, R$^2$=briged by (CH$_2$)$_4$, R$^3$=CH$_3$) and mixtures thereof.

It is preferred for the 2-aminoalkyl aryl ether (III) to be selected from the group comprising ketocaine (III; R= isopropyl, Ar=2-(1'-oxobutylphenyl)) and kinizocaine (III; R=CH$_2$, Ar=3-butyl-1-isoquinolyl).

It is preferred for the 2-aminoalkyl p-aminobenzoate (IV) to be selected from the group comprising procaine (IV; R=C$_2$H$_5$), R$^1$=H) and tetracaine (IV; R=CH$_3$, R$^1$=n-butyl).

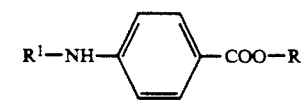

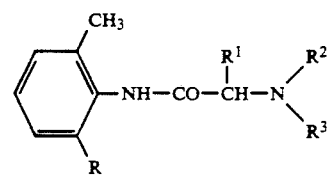

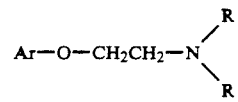

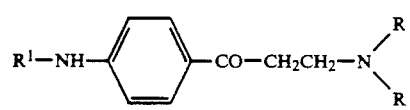

Especially preferred is lidocaine. Also preferred is prilocaine and lidocaine and prilocaine in admixture. The concentration of the active ingredient in the composition is preferred not to exceed 5% by weight for compositions to be applied to the skin; even more preferred is a concentration of between 0.3 and 3% by weight. In addition to the active ingredient, the composition with insect-repellent properties according to the invention comprises a carrier which may be an ointment, an emulsion, a cream, a fat oil or organic solvent or a solvent mixture. The composition according to the invention may also include a spray formulation.

The compositions according to the invention may incorporate a wide range of non-active ingredients used in formulating ointments, emulsions, creams, solutions or suspensions in fat oils, solutions in organic solvents or a solvent mixture, such as stabilizers, particularly antioxidants, colouring agents, fillers, bacteriostatic and anti-mold agents, emulsifiers, perfumes, vitamins, water repellents, humidifying agents, radiation absorbing agents, pH-controlling agents, gelling agents, surface tension modifying agents, etc. They may also include antibiotics and agents promoting wound healing, particularly for use in treating wounds in domestic amimals such as cattle or horses.

According to one aspect of the invention the composition may contain a salt of hyaluronic acid, particularly sodium hyaluronate. Especially preferred is a composition containing lidocaine and the sodium salt of hyaluronic acid.

No skin irritation has been noticed with the active compounds according to the invention. Neither is there any noticeable local anaesthetic effect since the active principle is being applied in low concentration and in vehicles that do not promote uptake by the skin. The mechanism of action of the local anaesthetic as a repellent agent has not been completely clarified. The fact that insects are only moderately deterred from landing on the skin but, once landed, do not suck blood, indicates that the mechanism is one different from known repellent agents such as DEET, which exhibit their effect in the gas phase like pheromones. The experiments show that the repellent effect is possessed by a wide range of class D local anaesthetics, i.e. compounds that exert their anaesthetic action by a combination of nerve membrane receptor dependent and receptor independent mechanism.

The invention will now be described in more detail by a number of examples. Percentages given are by weight.

EXAMPLE 1

| Spray solution. | |
|---|---|
| Prilocaine | 3.0% |
| Ethanol | 20.0% |
| Polyethylene glycol (MW 450) | 14.0% |
| Water | rest |

The above spray solution can be applied to the skin but may also be used for spraying other surfaces, such as the walls of cattle barns.

EXAMPLE 2

| Solution for application to the skin. | |
|---|---|
| Lidocaine | 1.0% |
| Polyethylene glycol (MW 450) | 99.0% |

This solution may, e.g., also be applied by brush to the walls of cattle barns.

EXAMPLE 3

| Fat oil solution. | |
|---|---|
| Prilocaine | 0,5% |
| Miglyol ® 812* | 99.5% |

*Reg. TM of Dynamit Nobel, Germany; fractionated coconut oil.

This fat oil solution can be applied to the skin and thereby acts both as a sun tan oil and insect repellent. Experiments have shown the oil to remain on the skin for a relatively long time.

EXAMPLE 4

| Ointment. | |
|---|---|
| Lidocaine | 2.5% |
| Lanogen ® *1500 | 67.5%. |
| Polyethylene glycol (MW 450) | 15.0% |
| Polypropylene glycol (MW 500) | 15.0% |

*Reg. TM of Hoechst, Germany; moisture-preserving polyethylene glycol.

Lidocaine is melted together with the other components and thoroughly mixed at 70° C. The shelf live of this ointment is at least 5 years if stored in an air-tight container. It is preferably used for application to the skin.

EXAMPLE 5

| Cream. | |
|---|---|
| Lidocaine | 2.5% |
| Prilocaine | 2.5% |
| Arlatone ® 289* | 1.9% |
| Carbopoly ® 934** | 1.0% |

| Cream. | |
|---|---|
| Water | rest |

*Reg. TM of Atlas-Chemie, Germany; non-ionic emulsifier; polyoxyethylene hydrogenated castor oil with about 50 moles of ethylene oxide per mole triglyceride.
**Reg. TM of Goodrich, U.S.; viscosity increasing agent; copolymerization product of polyacrylic acid with polyacrylsucrose.

Lidocaine, prilocaine and Arlatone ® are melted together, followed by addition of water. The blend is homogenized and mixed with pH-adjusted Carbopol ® gel giving the final product a pH of about 9.

EXAMPLE 6

| | |
|---|---|
| Lidocaine | 2.5% |
| Miglyol ® 812 | 6.9% |
| Arlatone ® 289 | 2.25% |
| Carbopol ® 934 | 1.0% |
| Water | rest |

A cream-like product similar to that of Example 5 is obtained.

EXAMPLE 7

Repellency test on *Aedes aegypti.*

The experiments were carried out with yellow-fever mosquitoes in an insectarium at +28° C. and at a relative humidity of 70%. The hands of the volunteer were washed and dried. Cream according to Example 5 was applied to one hand in an amount of 6,8 mg per cm$^2$. The treated hand was inserted into a net cage with about 30 starving female mosquitoes. After a conditioning period of one minute, the number of mosquitoes that flew onto the skin, rested on the skin and sucked during a period of one minute was recorded. The experiment was carried out after 0, 4, 6, and 8 hours, respectively, from the time when the cream was applied. The other hand was used as control. Results are summarized in Table 1.

TABLE 1

Repellency test of cream according to Example 5 with *Aedes aegypti*

| | Number of mosquitoes/min | | | | |
|---|---|---|---|---|---|
| Phase | control (at 0 h) | 0 h | 4 h | 6 h | 8 h |
| Landed on skin | 5 | 2 | 2 | 5 | 6 |
| Rested on skin | 6 | 1 | 6 | 17 | 17 |
| Sucked blood | 10 | 0 | 1 | 0 | 3 |

It is evident from the results that the cream according to Example 5 has a good repellent effect against *Aedes aegypti.*

EXAMPLE 8

In a competitive test carried out in an insectarium, pairs of compositions according to example 2 containing lidocaine, mepivacaine, etidocaine, prilocaine, tetracaine and ketocaine, respectively, were tested on rabbits for their relative effectiveness in an at +21° C. against *Culex pipiens.* Hair was removed by shaving corresponding left and right square dorsal areas 5×5 cm in size and the areas marked. One composition per area was applied and the animal was secured to pairs of windows in the insectarium matching in size and spatial orientation the shaved areas, thus providing access to these areas only. Feeding attempts on the respective area were registered during a period of 30 min. The following scale of decreasing effectivity was obtained: lidocaine≈prilocaine>mepivacaine≈tetracaine>bupivacaine>ketocaine>benzocaine. Whereas no feeding attempts were observed with lidocaine and prilocaine, benzocaine reduced the number of feeding attempts observed on an untreated area of the corresponding size by about 60%.

EXAMPLE 9

The ointment according to Example 5 was field-tested for protection of cattle wounds against gadflies (*Tabanus bovinus*). A substantial reduction in healing time (40%) was observed compared with wounds treated with ointment base corresponding to that of Example 5.

EXAMPLE 10

The repelling action of several active compounds according to the invention was investigated in a field study. White cardboard squares (60×60 cm) were sprayed with 95% ethanol (5 ml) containing 0.3 g of lidocaine, kinizocaine ketocaine and bupivacaine (II; $R=CH_3$, $R^1$, $R^2$=bridged by $(CH_2)_4$, $R^3$=n-butyl) respectively. A forth square (blank) was treated with ethanol only. The squares were allowed to dry for 10 min and placed vertically above the ground in a sparsely wooded lakeside area in central Sweden in early June (start at 2 p.m., observation time 30 min, clouded weather, air temperature 10° C., humidity 70%). The area was heavily infested with Aëdes species (predominantly *A. punctor* and *A. communis*). All repellent treated squares showed reduced landing frequency: lidocaine 27%, kinizocaine 35%, ketocaine 45%, bupivacaine 45% of blank landing frequency. Once landed, the mosquitoes seemed to stay for substantially shorter periods of time on the treated areas than on the blank area.

I claim:

1. A method of preventing mosquitoes from feeding on a human or non-human animal subject comprising applying to the skin of the subject a topical composition, comprising as the feeding preventive active ingredient from about 0.3 to about 5.0% by weight of a local anesthetic selected from the group consisting of lidocaine, prilocaine, etidocaine, mepivacaine, ketocaine, kinizocaine, procaine, tetracaine and mixtures thereof.

2. A method as described in claim 1 wherein said local anesthetic is lidocaine.

3. A method as described in claim 1 wherein said local anesthetic is a mixture comprising lidocaine and prilocaine.

4. A method as described in claim 1, wherein said composition contains from 0.3 to 3.0% by weight of said local anesthetic.

5. A method as described in claim 1 wherein said mosquitoes are selected from the group consisting of *Aedes aegypti, Culex pipiens, Aedes punctor* and *Aedes communis*.

6. A method as described in claim 5 wherein said mosquitoes are selected from the group consisting of *Aedes aegypti* and *Culex pipiens*.

7. A method as described in claim 1, wherein said composition further comprises an inert carrier selected from the group consisting of an ointment, emulsion, cream, fat oil, organic solvent, solvent mixture and spray formulation.

8. A method as described in claim 7, wherein said composition further comprises inactive ingredients selected from the group consisting of stabilizers, anti-oxidants, coloring agents, emulsifiers, perfumes, vitamins, water repellents, humidifying agents, radiation absorbing agents, fillers, bacteriostatic and anti-mold agents, gelling agents, viscosity controlling agents, pH-controlling agents, skin softening agents and surface tension modifying agents.

* * * * *